United States Patent
Hyodo et al.

(10) Patent No.: US 10,070,814 B2
(45) Date of Patent: Sep. 11, 2018

(54) MAGNETIC STIMULATION APPARATUS

(71) Applicant: NIHON KOHDEN CORPORATION, Tokyo (JP)

(72) Inventors: Akira Hyodo, Tokyo (JP); Takashi Kanno, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 252 days.

(21) Appl. No.: 15/042,864

(22) Filed: Feb. 12, 2016

(65) Prior Publication Data

US 2016/0235360 A1 Aug. 18, 2016

(30) Foreign Application Priority Data

Feb. 13, 2015 (JP) .................. 2015-026822

(51) Int. Cl.
| | |
|---|---|
| A61N 1/00 | (2006.01) |
| A61B 5/00 | (2006.01) |
| A61N 2/00 | (2006.01) |
| A61N 2/02 | (2006.01) |
| A61B 5/0408 | (2006.01) |
| A61B 5/0452 | (2006.01) |
| A61B 5/0492 | (2006.01) |
| A61B 5/1455 | (2006.01) |

(52) U.S. Cl.
CPC .......... *A61B 5/4836* (2013.01); *A61B 5/0408* (2013.01); *A61B 5/0452* (2013.01); *A61B 5/0492* (2013.01); *A61B 5/14551* (2013.01); *A61B 5/742* (2013.01); *A61N 2/006* (2013.01); *A61N 2/02* (2013.01)

(58) Field of Classification Search
CPC ........ A61B 5/4836; A61N 2/00; A61N 2/004; A61N 2/02
USPC .................................... 600/9–15
See application file for complete search history.

(56) References Cited

U.S. PATENT DOCUMENTS

| | | |
|---|---|---|
| 5,496,258 A | 3/1996 | Anninos et al. |
| 7,601,115 B2 | 10/2009 | Riehl |
| 2004/0019370 A1 | 1/2004 | Gliner et al. |
| 2005/0261542 A1 | 11/2005 | Riehl |
| 2006/0271108 A1 | 11/2006 | Libbus et al. |

(Continued)

FOREIGN PATENT DOCUMENTS

| | | |
|---|---|---|
| JP | 2008-500100 A | 1/2008 |
| JP | 2008-541850 A | 11/2008 |

(Continued)

OTHER PUBLICATIONS

European Search Report for EP 16 15 5451 dated Jun. 30, 2016.
Japanese Office action issued in Patent Application No. JP-2015-026822 dated Jun. 5, 2018.

*Primary Examiner* — John Lacyk
(74) *Attorney, Agent, or Firm* — Pearne & Gordon LLP

(57) ABSTRACT

A magnetic stimulator includes a coil which applies magnetic stimulation to a head of a living body, an intensity controller which controls an intensity of the magnetic stimulation applied by the coil, an acquiring section which acquires a biological signal from the living body, a detector which detects an adverse event of the living body from the biological signal acquired by the acquiring section, and an intensity suppressing section which, when an adverse event of the living body is detected by the detector, suppresses the intensity of the magnetic stimulation that is controlled by the intensity controller.

16 Claims, 8 Drawing Sheets

(56) References Cited

U.S. PATENT DOCUMENTS

| | | |
|---|---|---|
| 2009/0228079 A1 | 9/2009 | Libbus et al. |
| 2012/0041519 A1 | 2/2012 | Libbus et al. |
| 2012/0083700 A1 | 4/2012 | Osorio |
| 2012/0083701 A1 | 4/2012 | Osorio |
| 2012/0116183 A1 | 5/2012 | Osorio |
| 2012/0226108 A1 | 9/2012 | Osorio |
| 2012/0226168 A1 | 9/2012 | Osorio |
| 2012/0271372 A1 | 10/2012 | Osorio |
| 2012/0310050 A1 | 12/2012 | Osorio |
| 2013/0096363 A1 | 4/2013 | Schneider et al. |
| 2013/0096441 A1 | 4/2013 | Osorio |
| 2013/0150927 A1 | 6/2013 | Libbus et al. |
| 2013/0218233 A1 | 8/2013 | Warschewske et al. |
| 2013/0225992 A1 | 8/2013 | Osorio |
| 2013/0253353 A1 | 9/2013 | Kawamura |
| 2014/0243613 A1 | 8/2014 | Osorio |
| 2014/0276184 A1 | 9/2014 | Neuvonen |
| 2014/0371612 A1 | 12/2014 | Kawamura |
| 2015/0005592 A1 | 1/2015 | Osorio |
| 2015/0073237 A1 | 3/2015 | Osorio |
| 2015/0080670 A1 | 3/2015 | Osorio |
| 2015/0112410 A1 | 4/2015 | Libbus et al. |
| 2015/0196246 A1 | 7/2015 | Osorio |
| 2016/0038754 A1 | 2/2016 | Adjouadi et al. |
| 2016/0058359 A1 | 3/2016 | Osorio |
| 2016/0135727 A1 | 5/2016 | Osorio |
| 2017/0035368 A1 | 2/2017 | Osorio |
| 2017/0079573 A1 | 3/2017 | Osorio |
| 2017/0150916 A1 | 6/2017 | Osorio |
| 2018/0049704 A1 | 2/2018 | Osorio |
| 2018/0116580 A1 | 5/2018 | Osorio |

FOREIGN PATENT DOCUMENTS

| | | |
|---|---|---|
| JP | 5053080 B2 | 10/2012 |
| JP | 2013-529983 A | 7/2013 |
| JP | 2013-198562 A | 10/2013 |
| JP | 2013-538656 A | 10/2013 |
| WO | 92/03185 A1 | 3/1992 |
| WO | 2011/123548 A2 | 10/2011 |
| WO | 2014/145847 A1 | 9/2014 |

FIG. 4

|  | | HEART RATE | SpO2 | |
|---|---|---|---|---|
| ☐ Measure | | | | ✕ |
| Time | HR (Inst) | HR (Ave) | SpO2 | PR |
| 2014/10/29 16:08:33 | 95 | 94 | 97 | 94 |
| 2014/10/29 16:08:34 | 94 | 94 | 97 | 94 |
| 2014/10/29 16:08:35 | 95 | 94 | 97 | 94 |
| 2014/10/29 16:08:36 | 94 | 94 | 97 | 94 |
| 2014/10/29 16:08:37 | 94 | 94 | 96 | 94 |
| 2014/10/29 16:08:38 | 93 | 94 | 96 | 94 |
| 2014/10/29 16:08:39 | 93 | 94 | 96 | 94 |
| 2014/10/29 16:08:40 | 93 | 94 | 96 | 94 |
| 2014/10/29 16:08:41 | 93 | 94 | 96 | 94 |
| 2014/10/29 16:08:42 | 93 | 93 | 96 | 94 |
| 2014/10/29 16:08:43 | 94 | 93 | 96 | 94 |
| 2014/10/29 16:08:44 | 94 | 93 | 96 | 94 |
| 2014/10/29 16:08:45 | — | — | 96 | 94 |
| 2014/10/29 16:08:46 | 95 | 93 | 96 | 94 |
| 2014/10/29 16:08:47 | 94 | 93 | 96 | 94 |
| 2014/10/29 16:08:48 | 94 | 94 | 96 | 94 |
| 2014/10/29 16:08:49 | 94 | 94 | 96 | 94 |
| 2014/10/29 16:08:50 | 95 | 94 | 96 | 94 |
| 2014/10/29 16:08:51 | 95 | 94 | 96 | 94 |
| 2014/10/29 16:08:52 | 96 | 95 | 96 | 94 |
| 2014/10/29 16:08:53 | 95 | 95 | 96 | 94 |
| 2014/10/29 16:08:54 | 95 | 95 | 96 | 94 |

MAGNETIC STIMULATION APPARATUS

CROSS REFERENCE TO RELATED APPLICATION

This application is based on Japanese Patent Applications No. 2015-026822 filed on Feb. 13, 2015, the contents of which are incorporated herein by reference.

BACKGROUND

The presently disclosed subject matter relates to a magnetic stimulator which can noninvasively treat a neurological disease such as Parkinson disease and depression.

A neurological disease such as Parkinson disease or depression is treated by one of psychoanalysis therapy, pharmacologic therapy, and therapy in which the brain is directly stimulated. It is argued that, among such treatment methods, the therapy in which the brain is directly stimulated is particularly effective for treatment of a part of neurological diseases.

As a therapy in which the brain is directly stimulated, recently, a magnetic stimulation therapy which applies magnetic stimulation to a specific area of the brain of the patient is beginning to be used. The magnetic stimulation therapy is a treatment method in which an electric field is induced in the skull to stimulate a nerve. Tissues can be stimulated without dissipating the magnetic energy, and the brain can be stimulated more correctly and more surely (see Japanese Patent No. 5,053,080).

In the magnetic stimulation therapy, however, it is known that, in the case where treatment in which magnetic stimulation is applied at a high frequency of 1 Hz or higher is performed, there is a possibility that an epilepsy seizure occurs as a side effect depending on the patient.

The presently disclosed subject matter provides a magnetic stimulator in which, when an adverse event such as an epilepsy seizure is observed during treatment with a magnetic stimulation therapy, the treatment can be promptly suppressed, and a neurological disease can be noninvasively treated.

SUMMARY

A magnetic stimulator includes a coil which applies magnetic stimulation to a head of a living body, an intensity controller which controls an intensity of the magnetic stimulation applied by the coil, an acquiring section which acquires a biological signal from the living body, a detector which detects an adverse event of the living body from the biological signal acquired by the acquiring section, and an intensity suppressing section which, when an adverse event of the living body is detected by the detector, suppresses the intensity of the magnetic stimulation that is controlled by the intensity controller.

BRIEF DESCRIPTION OF DRAWINGS

FIG. 4 is a table illustrating values of a heart rate and SpO2 which are displayed on the displaying section shown in FIG. 1.

DETAILED DESCRIPTION OF EMBODIMENTS

Hereinafter, an embodiment of the magnetic stimulator of the presently disclosed subject matter will be described with reference to the drawings. The magnetic stimulator of the presently disclosed subject matter is effective for treatment of neurological diseases, particularly Parkinson disease.

Figure 1:
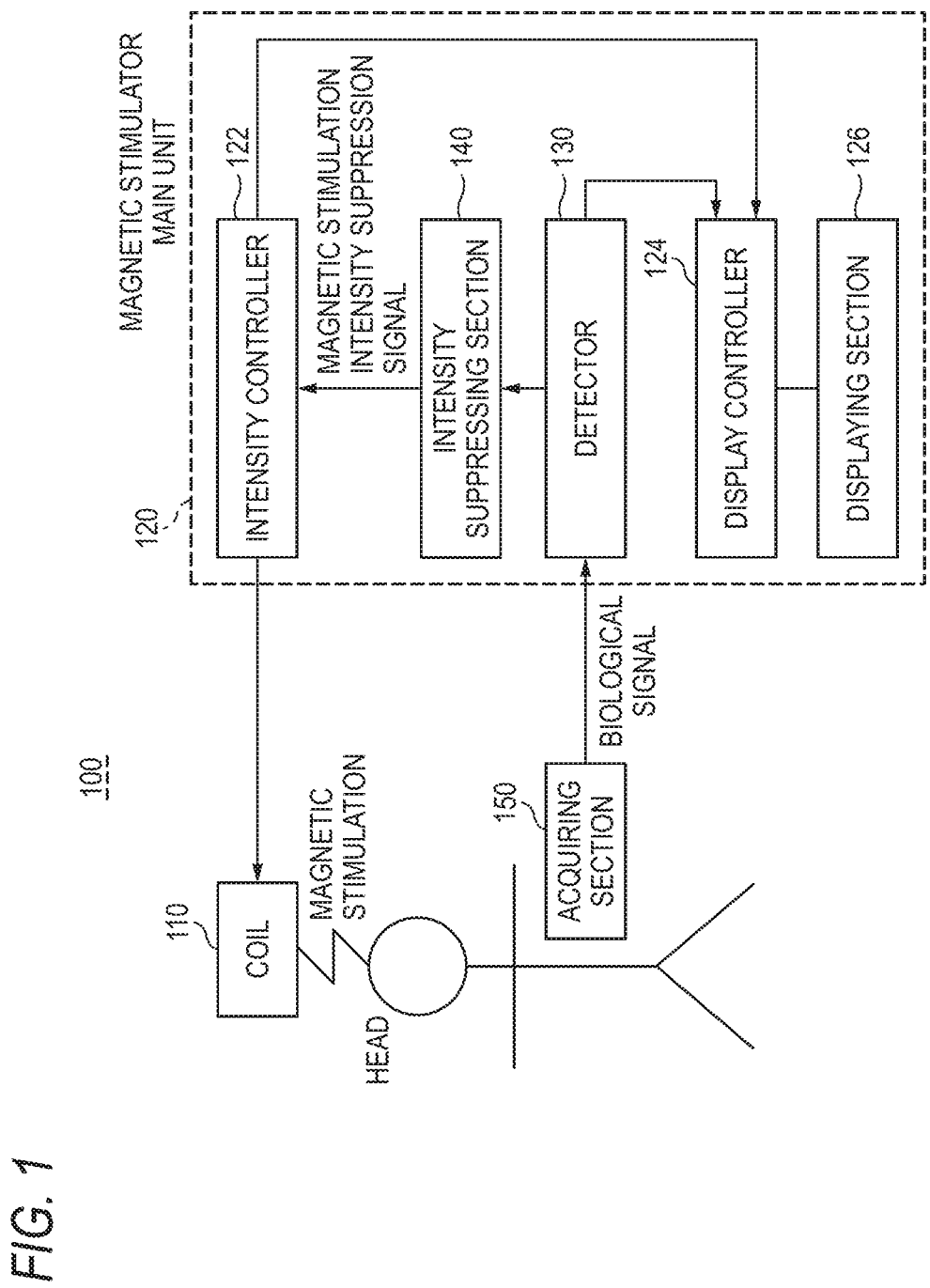
FIG. 1 illustrates a block diagram of a magnetic stimulator of an embodiment.

FIG. 1 is a block diagram of the magnetic stimulator of the embodiment. As shown in FIG. 1, the magnetic stimulator 100 of the embodiment can include a coil 110, a magnetic stimulator main unit 120, and an acquiring section 150.

The coil 110 applies magnetic stimulation to the head of a living body (patient). The magnetic stimulation must be correctly applied to a specific area of the head of the patient. Therefore, the coil 110 is fixed to an arm which is not shown, so that the coil 110 can be accurately positioned by the arm. The coil 110 may have any shape such as a circular shape, a figure of eight shape, or a conical shape. Depending on the employed shape, the shape of a magnetic field applied to the head is different. Therefore, the shape of the coil to be employed is selected in accordance with, for example, the kind of the neurological disease. A large current of several thousands of amperes is flown through the coil 110, and therefore a cooling device for cooling the coil 110 is attached to the periphery of the coil 110.

The acquiring section 150 acquires biological signals from the living body. Specifically, the acquiring section 150 acquires, as biological signals, an electrocardiogram (ECG) signal (for producing electrocardiogram (ECG) data) of the patient, the transmittances (for measuring the arterial oxygen saturation (hereinafter, referred to as SpO2)) of blood flowing through the fingertip of the patient with respect to red and infrared light beams, and a myoelectric signal (for producing electromyogram data) of the living body.

Although not illustrated, the magnetic stimulator main unit 120 can include a chair unit on which the patient under treatment sits, a control panel which accommodates electric components for supplying the large current to the coil 110, and a console which outputs various instructions to the control panel, and on which information transmitted from the control panel is displayed. The console may be configured by a personal computer (PC) which is usually used. By using the biological signals acquired by the acquiring section 150, the magnetic stimulator main unit 120 controls the intensity of the magnetic stimulation which is applied to the living body by the coil 110.

As shown in FIG. 1, the magnetic stimulator main unit 120 can include an intensity controller 122, a display controller 124, a displaying section 126, a detector 130, and an intensity suppressing section 140.

The intensity controller 122 controls the intensity of the magnetic stimulation which is applied by the coil 110. The intensity controller 122 changes the level of the current to be supplied to the coil 110, and the interval and time period of the current supply, thereby adjusting the intensity of the magnetic stimulation. The intensity controller 122 drives the coil 110 in a treatment mode in which the stimulation frequency (the number of stimulations per second, for example, five times (5 Hz)), the stimulation intensity (the percentage with respect to the motor threshold (the minimum intensity which can elicit muscle activity), for example, 32%), the duration time (the number of stimulation applications, for example, 50 times (10.0 sec.)), and the like are determined.

Preferably, the treatment mode is stored for each of the kinds of neurological diseases and patients, because treatment for a patient can be performed correctly and rapidly. The treatment mode is supplied to the display controller 124 which will be described later, and can be checked on the displaying section 126 which will be described later. The treatment mode is displayed in terms of the stimulation frequency, the stimulation intensity, the duration time, and the like.

The detector 130 detects or predicts an adverse event of the living body from the biological signals acquired by the acquiring section 150. In the case where the acquired biological signals include an ECG signal, the detector 130 produces ECG data by using the acquired ECG signal. The detector 130 detects or predicts an adverse event of the living body by using the produced ECG data. In the case where the acquired biological signals include the transmittances, the detector 130 measures the SpO2 by using the acquired transmittance. The detector 130 detects an adverse event of the living body by using the measured SpO2. In the case where the acquired biological signals include a myoelectric signal, the detector 130 produces electromyogram data by using the acquired myoelectric signal. Here, an adverse event means a symptom which impedes the continuation of the treatment, such as occurrence of an epilepsy seizure, occurrence of arrhythmia, or decrease of the SpO2.

The ECG data, the SpO2, or the electromyogram data are supplied to to the display controller 124 which will be described later, and can be checked on the displaying section 126 which will be described later. The ECG data are displayed as an ECG on the displaying section 126, and the electromyogram data are displayed as an electromyogram on the displaying section 126. The SpO2 is displayed as a numerical value on the displaying section 126. The condition of the patient under treatment is clearly known from the ECG and the SpO2. From the electromyogram, the operator can know whether the coil 110 is located at a position appropriate for treatment of the patient or not, and whether a spontaneous activity exists in the body of the patient or not.

When the detector 130 detects an adverse event of the living body, the intensity suppressing section 140 suppresses the intensity of the magnetic stimulation which is controlled by the intensity controller 122. When the detector 130 detects an adverse event, the intensity suppressing section 140 outputs a magnetic stimulation intensity suppression signal to the intensity controller 122. Upon reception of the magnetic stimulation intensity suppression signal, the intensity controller 122 suppresses the intensity of the magnetic stimulation. That is, the intensity controller 122 reduces the level of the current to be supplied to the coil 110, and the time period of the current supply, thereby reducing the intensity of the magnetic stimulation, or interrupts the current output to the coil 110 to stop the magnetic stimulation.

The display controller 124 causes at least one of the ECG data produced by the detector 130, the SpO2 measured by the detector, and the electromyogram data produced by the detector, to be displayed on the displaying section 126. Moreover, the display controller 124 causes the above-described treatment mode which is output from the intensity controller 122, to be displayed on the displaying section 126.

Figure 3:
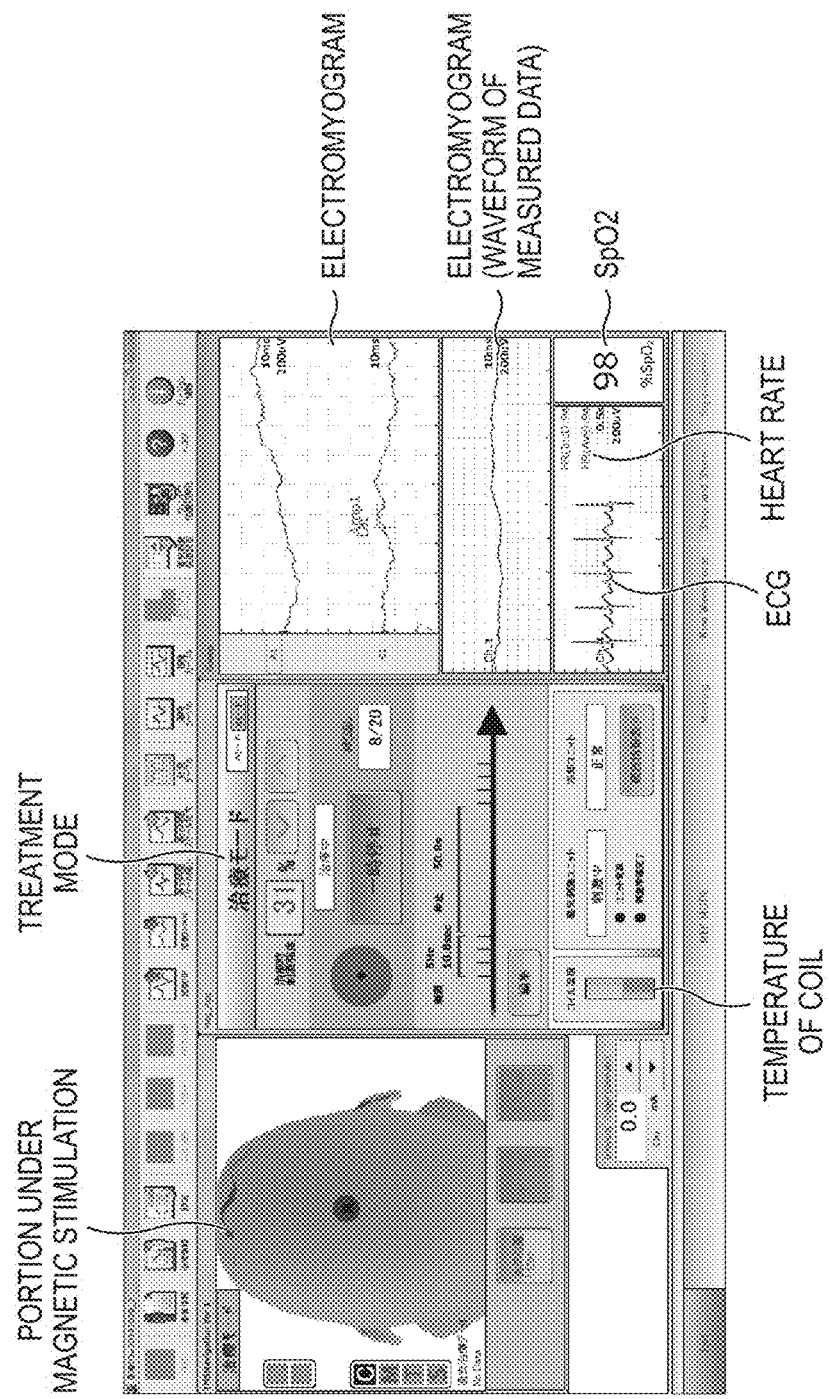
FIG. 3 is a view illustrating an example of a display performed by a displaying section shown in FIG. 1.

The displaying section 126 displays the ECG data, SpO2, electromyogram data, and treatment mode, and the like which have been described above. FIG. 3 illustrates an example of the display on the displaying section 126. The contents of the display will be described later.

The magnetic stimulator 100 of the embodiment approximately operates in the following manner. When treatment is started, the intensity controller 122 supplies a current in a predetermined treatment mode to the coil 110. This causes magnetic stimulation to be applied to the head of the patient. For example, a neurological disease such as Parkinson disease is treated by the magnetic stimulation.

During the treatment, the acquiring section 150 acquires biological signals (the ECG signal, the transmittances, and the electromyogram signal) of the patient, and the detector 130 detects an adverse event of the patient from the biological signals. If the detector 130 detects an adverse event such as "arrhythmia such as ventricular fibrillation or ventricular tachycardia," or predicts an adverse event such as "the patient will possibly have an epilepsy seizure," the intensity suppressing section 140 supplies the magnetic stimulation intensity suppression signal to the intensity controller 122 to suppress the intensity of the magnetic stimulation which is controlled by the intensity controller 122.

In treatment of a neurological disease such as Parkinson disease, an epilepsy seizure is recognized as a significant side effect. Therefore, the magnetic stimulator 100 of the embodiment is configured so as to be able to predict occurrence of a significant side effect such as an epilepsy seizure, and, when the occurrence is predicted, temporarily suppress the treatment. According to the configuration, the patient can safely receive the treatment.

The displaying section 126 displays the ECG data, the SpO2, the electromyogram data, the treatment mode, and the like. These data are displayed because, when the operator sees the display, the operator is enabled to easily know the situation of the treatment, and the condition of the patient under the treatment, and can supplementarily watch the security of the patient. The display on the displaying section 126 is performed in the manner shown in FIG. 3. The display manner will be described in detail later.

Figure 2:
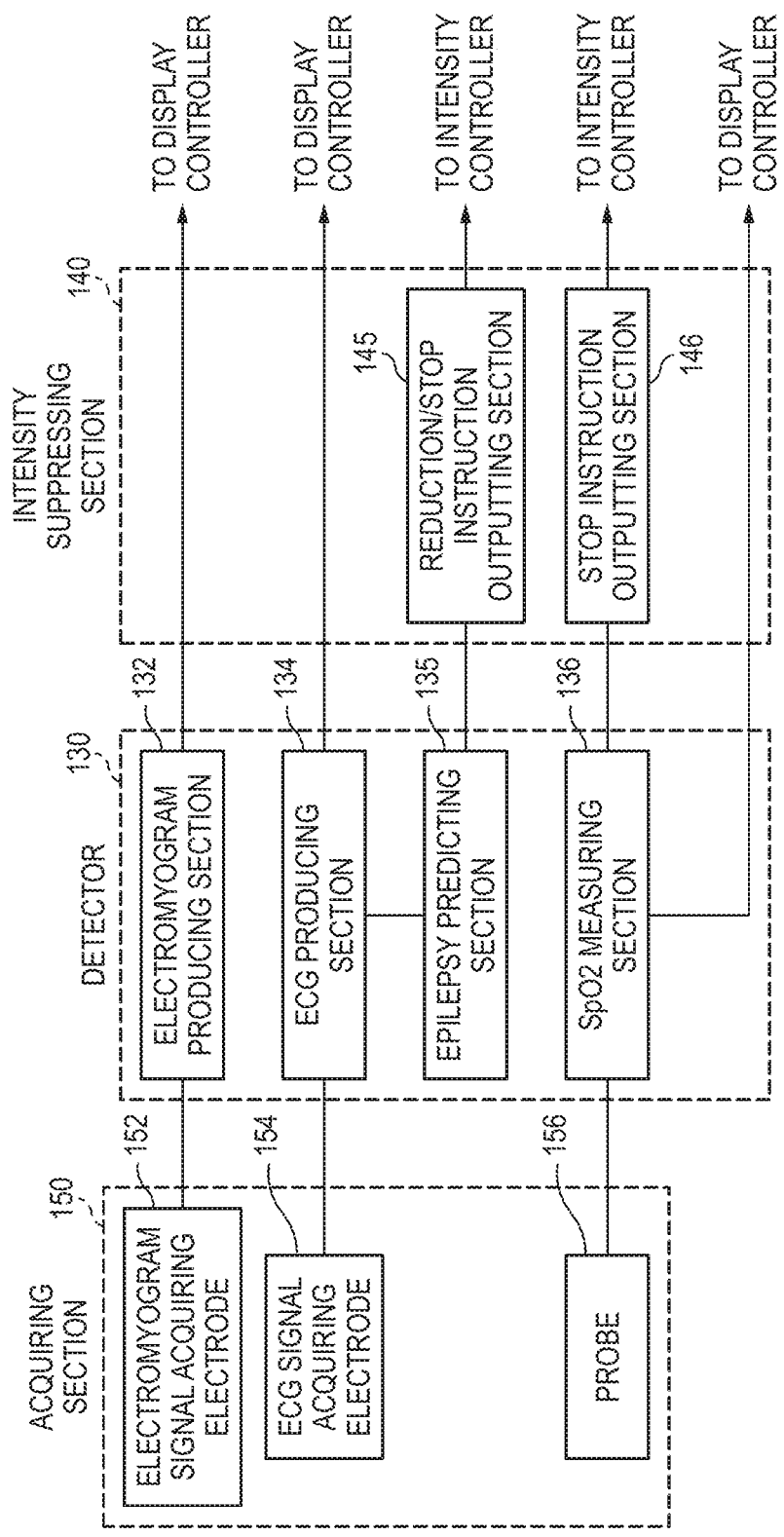
FIG. 2 illustrates a block diagram of an acquiring section, detector, and intensity suppressing section shown in FIG. 1.

FIG. 2 is a block diagram of the acquiring section 150, detector 130, and intensity suppressing section 140 which are shown in FIG. 1.

The acquiring section 150 can include electromyogram signal acquiring electrodes 152, ECG signal acquiring electrodes 154, and a probe 156.

The electromyogram signal acquiring electrodes 152 acquire the electromyogram signal of the living body. In order to correctly detect a muscle potential change appearing on the body surface, i.e., the muscle action potential, the electromyogram signal acquiring electrodes 152 are attached to the target muscle of the patient, respectively. The attachment of the electromyogram signal acquiring electrodes 152 is conducted because, when the motor evoked potential (MEP) is observed, it is possible to check whether the magnetic stimulation applied by the coil 110 gives magnetic stimulation to a portion which governs the body motion, and which is called the motor area of the brain or not. When magnetic stimulation is given with sufficient intensity to the motor area, the MEP is observed in the electromyogram shown on the displaying section 126 (see FIGS. 1 and 3).

The ECG signal acquiring electrodes 154 acquire the ECG signal of the living body. In order to obtain a 1-channel ECG, the ECG signal acquiring electrodes 154 are attached to, for example, the front arms, respectively. The attachment of the ECG signal acquiring electrodes 154 is conducted in order to predict an adverse event such as detection of arrhythmia or occurrence of an epilepsy seizure from the ECG data.

The probe 156 acquires the transmittances of blood flowing through the fingertip of the patient with respect to red and infrared light beams. In order to measure the arterial oxygen saturation (SpO2), the probe 156 is attached to the fingertip of the patient in a manner similar to the attachment of a clip. The attachment of the probe 156 is conducted in order to know an adverse event such as an abnormal decrease of the SpO2.

The detector 130 can include an electromyogram producing section 132, an ECG producing section 134, an epilepsy predicting section 135, and an SpO2 measuring section 136.

The electromyogram producing section 132 produces electromyogram data by using the electromyogram signal acquired by the electromyogram signal acquiring electrodes 152. The electromyogram data produced by the electromyogram producing section 132 are supplied to the display controller 124 (see FIG. 1). The display controller 124 causes the electromyogram data to be displayed on the displaying section 126 in the manner shown in FIG. 3 (see FIGS. 1 and 3).

The ECG producing section 134 produces ECG data by using the ECG signal acquired by the ECG signal acquiring electrodes 154. The produced ECG data are supplied to the epilepsy predicting section 135 which will be described later, so as to be used in prediction of an epilepsy seizure.

The ECG data produced by the ECG producing section 134 are supplied also to the display controller 124 (see FIG. 1). The display controller 124 causes the ECG data to be displayed on the displaying section 126 (see FIGS. 1 and 3). The ECG producing section 134 obtains not only waveform data but also the heart rate.

The epilepsy predicting section 135 predicts an epilepsy seizure by using the ECG data produced by the ECG producing section 134. When the epilepsy predicting section 135 predicts an epilepsy seizure, the section outputs a signal to a reduction/stop instruction outputting section 145 which will be described later. The technique for predicting an epilepsy seizure will be described in detail later.

The SpO2 measuring section 136 measures the SpO2 by using the transmittances of blood flowing through the fingertip of the patient with respect to red and infrared light beams. The transmittances are acquired by the probe 156. The SpO2 measuring section 136 supplies the measured SpO2 to a stop instruction outputting section 146. The SpO2 measuring section 136 further supplies the measured SpO2 value to the display controller 124, and the display controller 124 causes the SpO2 to be displayed on the displaying section 126 (see FIGS. 1 and 3).

The intensity suppressing section 140 can include the reduction/stop instruction outputting section 145 and the stop instruction outputting section 146.

The reduction/stop instruction outputting section 145 receives the signal which is output when the epilepsy predicting section 135 predicts an occurrence of an epilepsy seizure, and outputs reduction instructions or stop instructions as magnetic stimulation intensity suppressing instructions to the intensity controller 122, in order to reduce the intensity of the magnetic stimulation controlled by the intensity controller 122 (see FIG. 1), or stop the magnetic stimulation controlled by the intensity controller 122.

When the SpO2 measured by the SpO2 measuring section 136 becomes equal to or smaller than a preset threshold, the stop instruction outputting section 146 outputs the stop instructions to the intensity controller 122 in order to stop the magnetic stimulation controlled by the intensity controller 122.

FIG. 3 illustrates an example of a display performed by the displaying section 126 shown in FIG. 1.

In FIG. 3, the bright part of the head of the patient which is displayed in the left side is a portion to which the magnetic stimulation is applied by the coil 110. The upper middle part of FIG. 3 illustrates the treatment mode which is performed by the intensity controller 122 (see FIG. 1). In the figure, a mode where the stimulation intensity is 31%, the stimulation frequency is 5 Hz, and the duration time is 10 sec. is displayed. In FIG. 3, a bar graph like display is shown in the lower middle part. The display shows the temperature of the coil 110. It is seen that the temperature of the coil 110 is not exceed the certain value.

In FIG. 3, the two waveforms (MEPs) in the upper right side and denoted respectively as ELECTROMYOGRAM and ELECTROMYOGRAM (WAVEFORM OF MEASURED DATA) are electromyograms which are produced by the electromyogram producing section 132 based on the electromyogram data. When viewing the electromyograms, in the case where the waveforms are flat and do not largely fluctuate, it is seen that the magnetic stimulation applied by the coil 110 is not given to the motor area of the brain. Therefore, the electromyograms are used for determining whether the treatment portion is adequate or not. The electromyogram (waveform of measured data) shows the waveform of the electromyogram data themselves. Also the electromyogram (waveform of measured data) is displayed in order to enable the checking of whether a spontaneous activity exists in the body of the patient or not, to be performed.

In FIG. 3, the waveform in the lower right side and denoted as ECG is an ECG which is produced by the ECG producing section 134 based on the ECG data. Also the obtained heart rate is displayed on the right side of the ECG. Also the ECG and the heart rate are important indexes indicating the condition of the patient under treatment. When viewing the value of the SpO2 or the manner of variation of the heart rate, the operator can know the condition of the patient.

In FIG. 3, the numerical value 98 is the value of the SpO2 measured by the SpO2 measuring section 136. Also the value of the SpO2 is an important index indicating the condition of the patient under treatment. When viewing the transition of and manner of variation of the value of the SpO2, the operator can know the condition of the patient.

Figure 5:
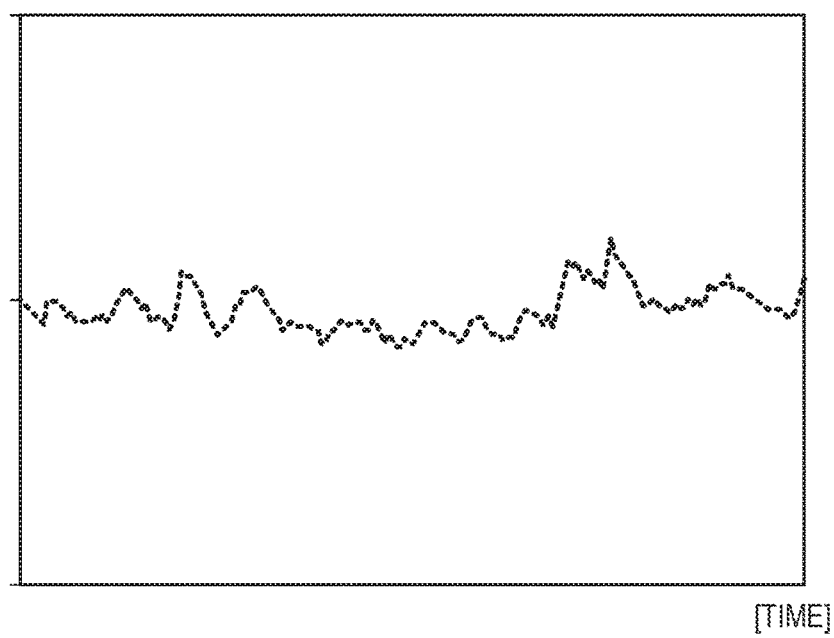
FIG. 5 is a graph illustrating heart beat variability which is displayed on the displaying section shown in FIG. 1.

The display controller 124 (see FIG. 1) may control the displaying section 126 so as to display not only the contents shown in FIG. 3, but also the values of the heart rate and SpO2 which are changed at every moment, as a numerical table of the heart rate and the SpO2 as shown in FIG. 4 (on the same screen as FIG. 3 or on another screen). Alternatively, the display controller 124 may control the displaying section 126 so as to display a graph such as shown in FIG. 5 in which the heart rate variability is graphically indicated (on the same screen as FIG. 3 or on another screen).

When the ECG, the heart rate, the SpO2, the electromyograms, and the like can be simultaneously displayed on the displaying section 126 as described above, it is possible to observe the condition of the autonomic nervous system from these displayed contents. From these displayed contents, the operator may possibly predict an adverse event such as an epilepsy seizure. When the condition of the patient is clinically known from these displayed contents, it is possible to warn of the condition of the patient, by using these displays.

Figure 6:
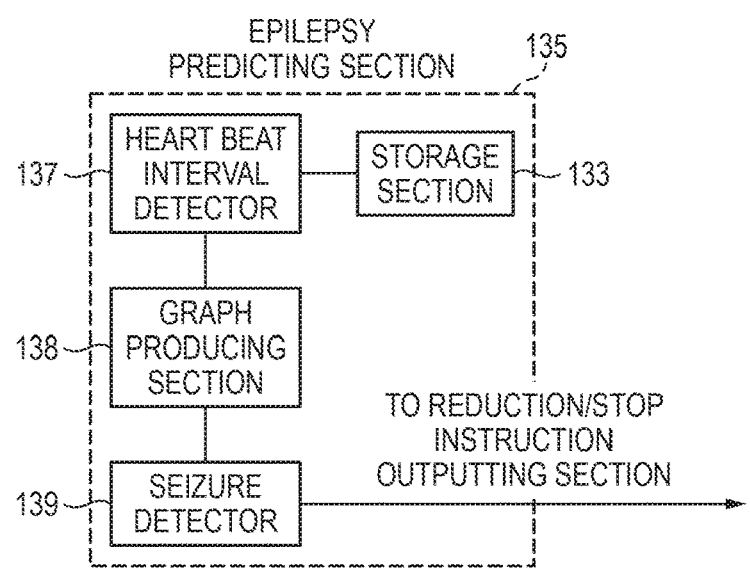
FIG. 6 illustrates a block diagram of an epilepsy predicting section shown in FIG. 2.

FIG. 6 is a block diagram of the epilepsy predicting section 135 shown in FIG. 2. The epilepsy predicting section 135 can include a storage section 133, a heart beat interval detector 137, a graph producing section 138, and a seizure detector 139.

The storage section 133 stores the ECG data produced by the ECG producing section 134 (see FIG. 2). The stored ECG data are used in detection of the heart beat interval RR by the heart beat interval detector 137.

The heart beat interval detector 137 detects the heart beat interval RR by using the ECG data. The heart beat interval RR is detected by once storing the ECG data in the storage section 133, calculating peaks of adjacent R waves in the stored ECG data, and obtaining the interval between the R waves.

The graph producing section 138 produces a Poincare plotted graph based on the heart beat interval RR which is continuously detected for each heart beat by the heart beat interval detector 137. Namely, the graph producing section 138 produces Poincare plots by sequentially plotting heart beat intervals in a two-dimensional orthogonal graph while the heart beat interval $RR_n$ at an arbitrary timing in consecutive heart beats is set as a lateral coordinate, and the next heart beat interval $RR_{n+1}$ is set as a vertical coordinate.

Poincare plots are plots in which, in consecutive heart beats, heart beat intervals are sequentially plotted in a two-dimensional orthogonal graph while the heart beat interval $RR_n$ at an arbitrary timing is set as the abscissa, and the next heart beat interval $RR_{n+1}$ is set as the ordinate. The heart beat interval RR means the time difference between the peak of the R wave at an arbitrary timing in an ECG, and that of the next R wave. The suffix n of the heart beat interval $RR_n$ means the order of the heart beat interval RR, and the heart beat interval $RR_{n+1}$ indicates the next heart beat interval subsequent to the heart beat interval $RR_n$.

The seizure detector 139 detects an epilepsy seizure based on the graph of Poincare plots produced by the graph producing section 138. The method of detecting an epilepsy seizure by the seizure detector 139 will be described later. When an epilepsy seizure is detected, the seizure detector 139 outputs a signal to the reduction/stop instruction outputting section 145 (see FIG. 2).

Figure 7:
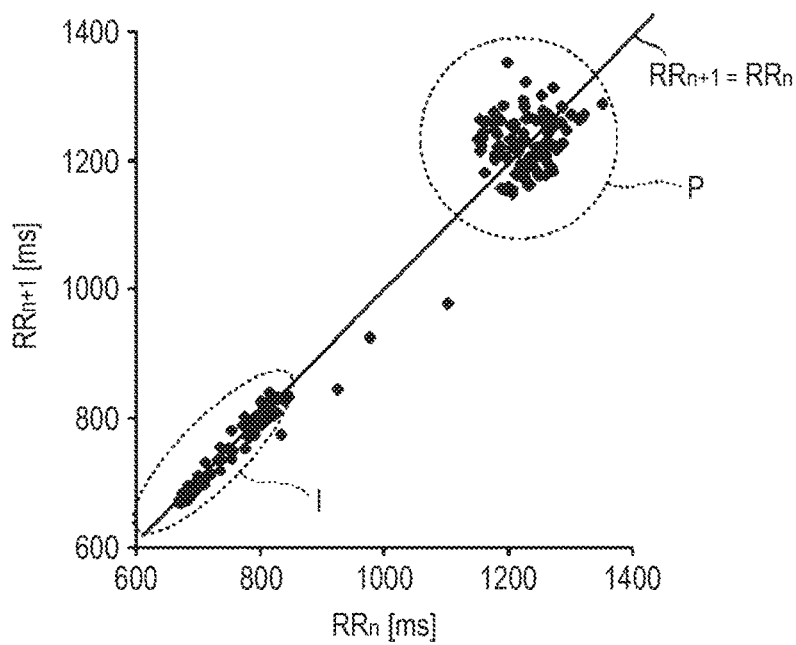
FIG. 7 is a view illustrating a graph in which Poincare plots are generated before and after an occurrence of an epilepsy seizure.

FIG. 7 is a view showing a graph in which Poincare plots are generated before and after an occurrence of an epilepsy seizure. In the graph shown in FIG. 7, the abscissa indicates the heart beat interval $RR_n$ which is obtained from the ECG, and the ordinate indicates the next heart beat interval $RR_{n+1}$ which is obtained from the ECG, and which is temporally adjacent to the heart beat interval $RR_n$.

The Poincare plots enclosed by the broken line P in FIG. 7 are Poincare plots before the occurrence of an epilepsy seizure, and those enclosed by the broken line I are Poincare plots after the occurrence of the epilepsy seizure.

As seen from the graph of FIG. 7, when an epilepsy seizure is detected, the heart beat interval RR is rapidly shortened, and the fluctuation which is the width of distribution of Poincare plots in the direction vertical to the straight line $RR_{n+1}=RR_n$ is decreased. Namely, when an epilepsy seizure is not detected, Poincare plots form a loose cluster in the upper right side of the graph of FIG. 7, and, when an epilepsy seizure is detected, the Poincare plots rapidly move to the lower left side to converge into the vicinity of the straight line $RR_{n+1}=RR_n$. In FIG. 7, the straight line $RR_{n+1}=RR_n$ is shown in the graph, but the straight line may not be shown in the graph.

In the embodiment, an epilepsy seizure is predicted based on two phenomena caused by detection of an epilepsy seizure, i.e., a phenomenon in which the heart beat interval RR is shortened, and that in which the fluctuation of Poincare plots is decreased. When an epilepsy seizure is predicted by using the two characteristic phenomena, an epilepsy seizure can be detected without erroneous detection and highly sensitively.

Figure 8:
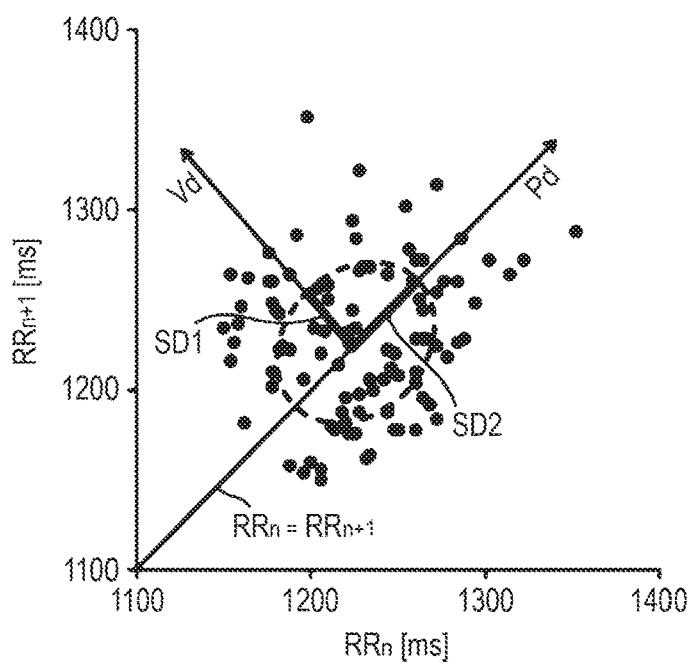
FIG. 8 is a view illustrating parameters which are used in the case where a seizure detector shown in FIG. 6 predicts an epilepsy seizure.

FIG. 8 is a view illustrating parameters which are used in the case where the seizure detector 139 predicts an epilepsy seizure. In the graph shown in FIG. 8, similarly with FIG. 7, the abscissa indicates the heart beat interval $RR_n$ which is obtained from the ECG, and the ordinate indicates the next heart beat interval $RR_{n+1}$ which is obtained from the ECG, and which is temporally adjacent to the heart beat interval $RR_n$.

The dots shown in FIG. 8 are Poincare plots, and the straight line $RR_{n+1}=RR_n$ is also shown. The arrow Vd shown in FIG. 8 indicates the direction vertical to the straight line $RR_{n+1}=RR_n$, and SD1 which is indicated by the thick line on the arrow Vd indicates the standard deviation of the distribution of Poincare plots in the direction of the arrow Vd. The arrow Pd shown in FIG. 8 indicates the direction parallel to the straight line $RR_{n+1}=RR_n$, and SD2 which is indicated by the thick line on the arrow Pd indicates the standard deviation of the distribution of Poincare plots in the direction of the arrow Pd.

The seizure detector 139 detects an epilepsy seizure based on the standard deviation SD1 (hereinafter, referred to simply as "SD1 value") of the distribution of Poincare plots in the direction Vd vertical to the straight line $RR_{n+1}=RR_n$, and the standard deviation SD2 (hereinafter, referred to simply as "SD2 value") of the distribution of Poincare plots in the direction Pd parallel to the straight line $RR_{n+1}=RR_n$. Specifically, the seizure detector 139 detects an epilepsy seizure based on a change of a value (hereinafter, referred to merely as "SD1/SD2 ratio") which is obtained by dividing the SD1 value by the SD2 value. The seizure detector 139 compares the presently calculated SD1/SD2 ratio with the previously calculated SD1/SD2 ratio, and, if it is determined that there is a significant difference, can detect an epilepsy seizure.

When an epilepsy seizure is detected based on a change of the SD1/SD2 ratio as described above, the rate of erroneous detection of an epilepsy seizure can be further lowered, and the detection sensitivity can be more improved.

Preferably, a threshold for detecting an epilepsy seizure from a change of the SD1/SD2 ratio is set for each subject. This can further improve the sensitivity of detection of an epilepsy seizure.

An adequate weight may be applied to the SD1 value or SD2 value which provides the SD1/SD2 ratio.

Alternatively, the seizure detector 139 may detect an epilepsy seizure based on a situation where the SD1 value is equal to or smaller than a preset threshold, and the SD2 value is equal to or larger than a preset threshold. Namely, individual thresholds may be set for the SD1 value and the SD2 value, respectively, and, when the both values exceed the thresholds, an epilepsy seizure may be detected.

Alternatively, an epilepsy seizure may be detected based on a change of a value which is obtained by dividing the SD2 value by the SD1 value.

Figure 9:
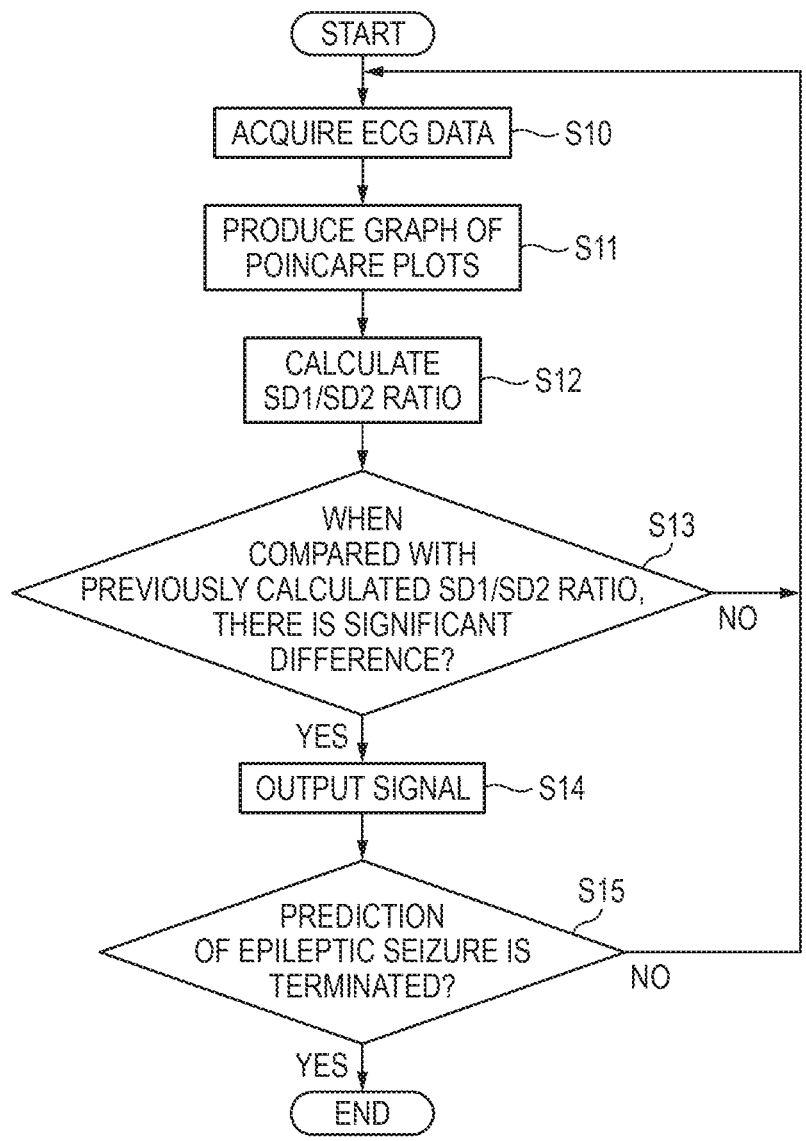
FIG. 9 illustrates an operation flowchart of the epilepsy predicting section of FIG. 6.

FIG. 9 is an operation flowchart of the epilepsy predicting section 135 of FIG. 6.

The heart beat interval detector 137 receives ECG data from the ECG producing section 134 (step S10). The received ECG data are temporarily stored in the storage section 133.

The heart beat interval detector 137 detects the heart beat interval RR by using the ECG data stored in the storage section 133, and the graph producing section 138 produces a graph of Poincare plots by using the detected heart beat interval RR (step S11).

The seizure detector 139 calculates the SD1/SD2 ratio based on the Poincare plots produced by the graph producing section 138 (step S12). The seizure detector 139 compares the previously calculated SD1/SD2 ratio with the presently calculated SD1/SD2 ratio, and determines whether there is a significant difference or not (step S13).

If, in the comparison between the previously calculated SD1/SD2 ratio and the presently calculated SD1/SD2 ratio, it is determined that there is no significant difference (step S13: NO), steps S10 to S13 are repeated.

If it is determined that there is a significant difference in the comparison between the previously calculated SD1/SD2 ratio and the presently calculated SD1/SD2 ratio, the seizure detector 139 outputs a signal toward the reduction/stop instruction outputting section 145 (see FIG. 2) (step S14).

The processes of steps S10 to S15 are repeated until instructions for terminating the prediction of an epilepsy seizure are issued (step S15: NO). If the instructions for terminating the prediction of an epilepsy seizure are issued (step S15: YES), the processes of steps S10 to S15 are ended.

In the magnetic stimulator 100 of the embodiment, the treatment safety is largely affected by the accuracy of prediction of an epilepsy seizure. Therefore, the accuracy of prediction of an epilepsy seizure was checked in the following example.

Example

An example of the embodiment will be described.
[Conditions and Method]

(a) Subjects: 19 persons (15 males) of ages 19 to 67.

(b) With respect to 19 epilepsy seizures of refractory temporal lobe epilepsy, the heart beat interval RR was measured by using ECG s generated by an electrocardiograph having a sampling frequency of 200 Hz or 500 Hz. Poincare plots were generated, and the SD1/SD2 ratios were calculated.

(c) It was considered whether differences of averages of SD1 value, SD2 value, and the SD1/SD2 ratio before and after a seizure are significant or not.

The p-value shown in Table 1 below indicates the probability that, in the case where a null hypothesis that there is no difference in SD1 value, SD2 value, and the SD1/SD2 ratio before and after an occurrence of an epilepsy seizure is generated, measured data are incidentally consistent with the null hypothesis.

[Results]

Table 1 below shows the SD1 value, SD2 value, and SD1/SD2 ratio which were measured in the example, and the p-value.

TABLE 1

| | Before epilepsy seizure | After epilepsy seizure | p-value |
|---|---|---|---|
| SD1 value [ms] | 33.3 ± 30.2 | 11.0 ± 4.3 | 0.004 |
| SD2 value [ms] | 74.4 ± 49.0 | 117.1 ± 50.6 | 0.012 |
| SD1/SD2 ratio | 0.46 ± 0.27 | 0.11 ± 0.06 | <0.001 |

As shown in Table 1, it has been proven that the difference between the SD1/SD2 ratios before and after an occurrence of an epilepsy seizure is significant, and an epilepsy seizure can be sufficiently detected based on a change of the SD1/SD2 ratio.

In the above, the functions of the components of the magnetic stimulator 100 of the embodiment have been described in detail. Next, the operation of the whole magnetic stimulator 100 of the embodiment will be described.

Figure 10:
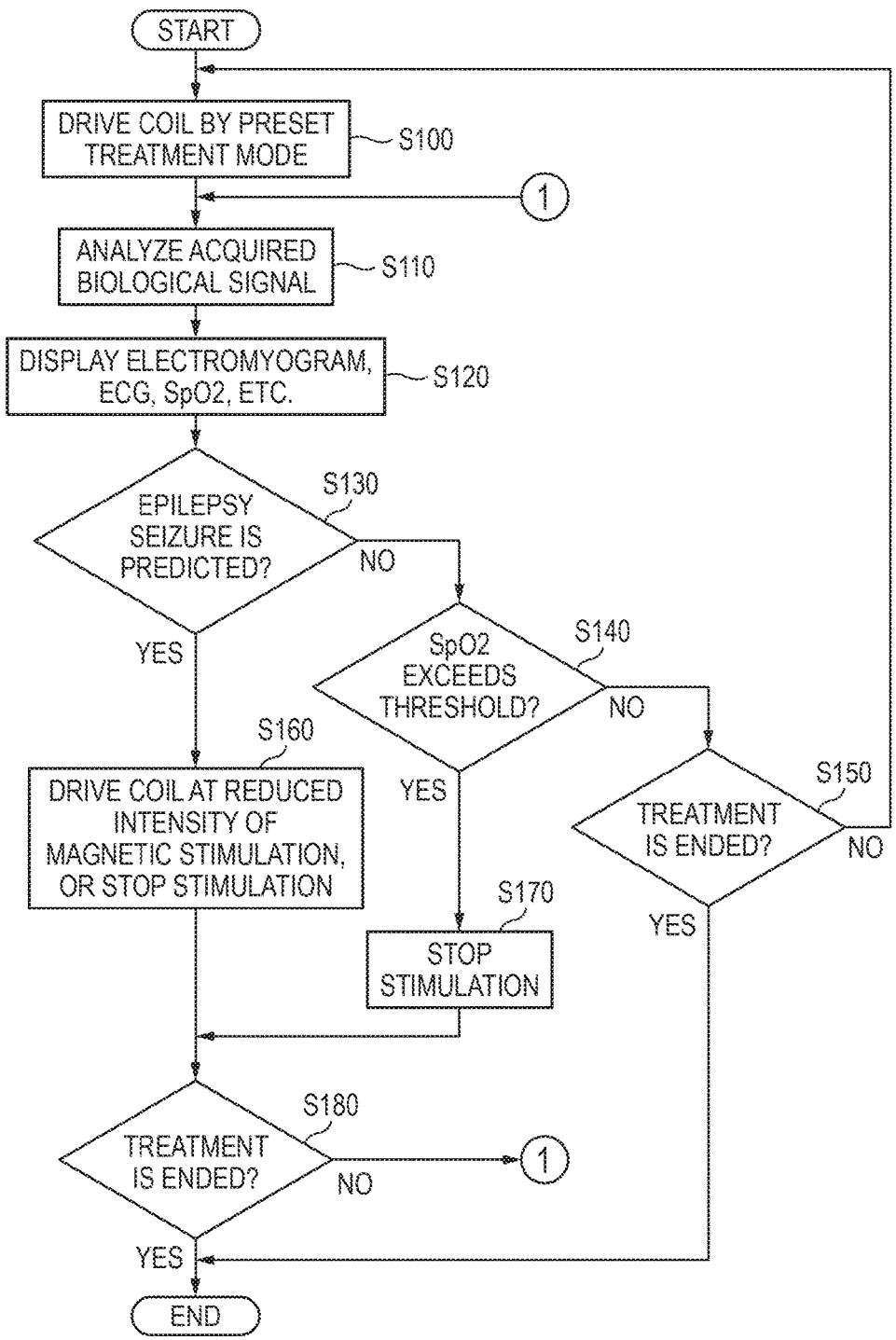
FIG. 10 illustrates an operation flowchart of the magnetic stimulator of the embodiment.

FIG. 10 is an operation flowchart of the magnetic stimulator 100 of the embodiment.

Before the start of treatment by the magnetic stimulation therapy, the operator accurately sets the position of the coil 110 (see FIG. 1) to that adequate for treatment of the symptom of the patient. From the display (the portion under magnetic stimulation) of the displaying section 126, it is possible to check whether the position of the coil 110 is adequate or not.

When the treatment is started, the intensity controlling section 122 drives the coil 110 by the preset treatment mode. This causes an electric field to be induced in the skull of the patient by the coil 110 (step S100).

The detector 130 analyzes the biological signals acquired by the acquiring section 150. Specifically, the electromyogram producing section 132 (see FIG. 2) processes the myoelectric signal acquired from the electromyogram signal acquiring electrodes 152, the ECG producing section 134 processes the ECG signal acquired from the ECG signal acquiring electrodes 154, and the SpO2 measuring section 136 measures the SpO2 from the transmittances acquired from the probe 156 (step S110).

The display controller 124 causes the electromyogram data produced by the electromyogram producing section 132, the ECG data produced by the ECG producing section 134, the SpO2 measured by the SpO2 measuring section 136, and the like to be displayed on the displaying section 126 (step S120).

The detector 130 determines whether an epilepsy seizure is predicted by the epilepsy predicting section 135 or not (step S130).

If an epilepsy seizure is not predicted (step S130: NO), the detector 130 then determines whether the SpO2 exceeds the threshold or not (step S140).

If the SpO2 does not exceed the threshold (step S140: NO), the magnetic stimulator main unit 120 determines whether the treatment is ended or not (step S150).

If an epilepsy seizure is not predicted by the epilepsy predicting section 135 (step S130: NO), and the SpO2 does not exceed the threshold (step S140: NO), the processes of steps S100 to S150 are repeated until the treatment is ended.

If an epilepsy seizure is not predicted by the epilepsy predicting section 135 (step S130: NO), the SpO2 does not exceed the threshold (step S140: NO), and the treatment is ended (step S150: YES), the magnetic stimulator main unit 120 terminates the treatment.

By contrast, if an epilepsy seizure is predicted by the epilepsy predicting section 135 (step S130: YES), the reduction/stop instruction outputting section 145 outputs the magnetic stimulation intensity suppression signal (reduction instructions or stop instructions) to the intensity controller 122. The intensity controller 122 drives the coil 110 at the reduced intensity of magnetic stimulation, or stops the current supply to the coil 110 (step S160).

If an epilepsy seizure is not predicted by the epilepsy predicting section 135 (step S130: NO), but the SpO2 exceeds the threshold (step S140: YES), the stop instruction outputting section 146 outputs the magnetic stimulation intensity suppression signal (stop instructions) to the intensity controller 122. The intensity controller 122 stops the current supply to the coil 110 (step S170).

The magnetic stimulator main unit 120 determines whether the treatment is ended or not (step S180). If the treatment is not ended (step S180: NO), the processes of steps S110 to S180 are performed. If the treatment is ended (step S180: YES), the magnetic stimulator main unit 120 terminates the treatment.

The magnetic stimulator 100 of the embodiment achieves the following effects.

In the embodiment, when an adverse event such as occurrence of an epilepsy seizure, occurrence of arrhythmia, or reduction of the SpO2 is predicted or detected, the intensity of the magnetic treatment is reduced or the magnetic treatment is stopped. Therefore, safe treatment can be performed on the patient.

In the embodiment, the position of the coil 110 with respect to the head of the patient, and electromyograms can be displayed on the displaying section 126. When viewing the waveforms of the electromyograms, therefore, the operator can easily know whether the coil 110 is located at a position appropriate for treatment of the patient or not, and whether a spontaneous activity exists in the body of the patient or not.

In the embodiment, the electromyograms, the ECG, the SpO2, the treatment mode, and the like can be simultaneously displayed on the displaying section 126. When viewing these displays, the operator can monitor the condition of the patient under treatment. Therefore, safer treatment can be performed.

In the embodiment, when an adverse event such as an epilepsy seizure is observed during treatment of a neurological disease such as Parkinson disease or depression, the treatment can be promptly suppressed, and the neurological disease can be safely treated.

Although, in the embodiment, treatment of Parkinson disease has been exemplarily described, the magnetic stimulator of the embodiment may be effective in treatment of not only Parkinson disease but also other diseases such as major depressive disorder, epilepsy, schizophrenia, Tourette syndrome, amyotrophic lateral sclerosis (ALS), multiple sclerosis (MS), Alzheimer disease, attention deficit/hyperactivity disorder, obesity, bipolar disorder/mania, anxiety disorders (panic disorder with and without agoraphobia, social phobia also known as social anxiety disorder, acute stress disorder, generalized anxiety disorder), post-traumatic stress disorder (one of anxiety disorders in DSM), obsessive compulsive disorder (one of anxiety disorders in DSM), aching pain (migraine, trigeminal neuralgia) (also chronic pain disorders such as neuropathic pain, e.g., pain due to diabetic neuropathy, post-herpetic neuralgia, e.g., fibromyalgia, and regional myofascial pain syndromes), rehabilitation following stroke (neuro plasticity induction), tinnitus, stimulation of implanted neurons to facilitate integration, substance-related disorders (dependence, abuse, and withdrawal diagnoses for alcohol, cocaine, amphetamine, caffeine, nicotine, and cannabis), spinal cord injury and regeneration/rehabilitation, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, and eating disorders (bulimia, anorexia, binge eating).

What is claimed is:

1. A magnetic stimulator comprising:
    a coil which applies magnetic stimulation to a head of a living body;
    an intensity controller which controls an intensity of the magnetic stimulation applied by the coil;
    an acquiring section which acquires a biological signal from the living body;
    a detector which detects an adverse event of the living body from the biological signal acquired by the acquiring section; and
    an intensity suppressing section which, when an adverse event of the living body is detected by the detector, suppresses the intensity of the magnetic stimulation that is controlled by the intensity controller, wherein:
    the acquiring section includes electrocardiogram signal acquiring electrodes which acquire an electrocardiogram signal of the living body,
    the detector includes:
        an electrocardiogram producing section which produces electrocardiogram data by using the electrocardiogram signal acquired by the electrocardiogram signal acquiring electrodes; and
        an epilepsy predicting section which predicts an epilepsy seizure by using the electrocardiogram data produced by the electrocardiogram producing section,
    the intensity suppressing section includes a reduction/stop instruction outputting section which, when the epilepsy predicting section predicts an epilepsy seizure, outputs a magnetic stimulation intensity suppression signal to the intensity controller, the magnetic stimulation intensity suppression signal being configured to cause the intensity controller to reduce the intensity of the magnetic stimulation controlled by the intensity controller, or to stop the magnetic stimulation controlled by the intensity controller,
    the acquiring section includes a probe which acquires transmittances of blood of the living body with respect to red and infrared light beams,
    the detector includes an arterial oxygen saturation (SpO2) measuring section which measures an SpO2 by using the transmittances acquired by the probe,
    the intensity suppressing section includes a stop instruction outputting section which, when the SpO2 measured by the SpO2 measuring section is equal to or less than a preset threshold, outputs stop instructions as magnetic stimulation intensity suppressing instructions to the intensity controller, the magnetic stimulation intensity suppressing instructions being configured to cause the intensity controller to stop the magnetic stimulation controlled by the intensity controller, and
    the detector is configured to determine whether the SpO2 exceeds the preset threshold or not, when the epilepsy seizure is not predicted by the epilepsy predicting section.

2. The magnetic stimulator according to claim 1, wherein the epilepsy predicting section includes a storage section which stores the electrocardiogram data produced by the electrocardiogram producing section,
- a heart beat interval detector which detects heart beat intervals of consecutive heart beats by using the electrocardiogram data stored in the storage section,
- a graph producing section which produces Poincare plots by sequentially plotting the beat intervals of consecutive heart beats detected by the heart beat interval detector, in a two-dimensional orthogonal graph while a heart beat interval at an arbitrary timing is set as a lateral coordinate, and a next heart beat interval is set as a vertical coordinate, and
- a seizure detecting section which detects an epilepsy seizure by, in a graph of Poincare plots produced by the graph producing section, using a change of a distribution of a group of the plotted values in a direction vertical to a straight line passing an origin and a point where the lateral and vertical coordinates are equal to each other, and a change of a distribution in a direction parallel to the straight line.

3. The magnetic stimulator according to claim 2, wherein the seizure detecting section predicts an epilepsy seizure based on a change of an SD1/SD2 ratio which is a ratio of a standard deviation SD2 in the parallel direction to a standard deviation SD1 in the vertical direction.

4. The magnetic stimulator according to claim 2, wherein the seizure detecting section predicts an epilepsy seizure when an SD1/SD2 ratio which is a ratio of a standard deviation SD2 in the parallel direction to a standard deviation SD1 in the vertical direction is equal to or smaller than a preset threshold.

5. The magnetic stimulator according to claim 1, wherein the acquiring section includes electrocardiogram signal acquiring electrodes which acquire an electrocardiogram signal of the living body,
- the detector includes an electrocardiogram producing section which produces electrocardiogram data by using the electrocardiogram signal acquired by the electrocardiogram signal acquiring electrodes, and detects arrhythmia by using the electrocardiogram data produced by the electrocardiogram producing section, and
- the intensity suppressing section includes a reduction/stop instruction outputting section which, when the detector detects arrhythmia, outputs magnetic stimulation intensity suppressing instructions to the intensity controller, the magnetic stimulation intensity suppressing instructions being configured to cause the intensity controller to reduce the intensity of the magnetic stimulation controlled by the intensity controller, or to stop the magnetic stimulation controlled by the intensity controller.

6. The magnetic stimulator according to claim 1, wherein the acquiring section further includes electromyogram signal acquiring electrodes which acquire an electromyogram signal of the living body, and
- the detector further includes an electromyogram producing section which produces electromyogram data by using the electromyogram signal acquired by the electromyogram signal acquiring electrodes.

7. The magnetic stimulator according to claim 2, wherein the acquiring section further includes electromyogram signal acquiring electrodes which acquire an electromyogram signal of the living body, and
- the detector further includes an electromyogram producing section which produces electromyogram data by using the electromyogram signal acquired by the electromyogram signal acquiring electrodes.

8. The magnetic stimulator according to claim 3, wherein the acquiring section further includes electromyogram signal acquiring electrodes which acquire an electromyogram signal of the living body, and
- the detector further includes an electromyogram producing section which produces electromyogram data by using the electromyogram signal acquired by the electromyogram signal acquiring electrodes.

9. The magnetic stimulator according to claim 4, wherein the acquiring section further includes electromyogram signal acquiring electrodes which acquire an electromyogram signal of the living body, and
- the detector further includes an electromyogram producing section which produces electromyogram data by using the electromyogram signal acquired by the electromyogram signal acquiring electrodes.

10. The magnetic stimulator according to claim 5, wherein the acquiring section further includes electromyogram signal acquiring electrodes which acquire an electromyogram signal of the living body, and
- the detector further includes an electromyogram producing section which produces electromyogram data by using the electromyogram signal acquired by the electromyogram signal acquiring electrodes.

11. The magnetic stimulator according to claim 6, wherein the magnetic stimulator further includes a display controller which causes at least one of the electrocardiogram data produced by the detector, the SpO2 measured by the detector, and the electromyogram data produced by the detector, to be displayed on a displaying section.

12. The magnetic stimulator according to claim 7, wherein the magnetic stimulator further includes a display controller which causes at least one of the electrocardiogram data produced by the detector, the SpO2 measured by the detector, and the electromyogram data produced by the detector, to be displayed on a displaying section.

13. The magnetic stimulator according to claim 8, wherein the magnetic stimulator further includes a display controller which causes at least one of the electrocardiogram data produced by the detector, the SpO2 measured by the detector, and the electromyogram data produced by the detector, to be displayed on a displaying section.

14. The magnetic stimulator according to claim 9, wherein the magnetic stimulator further includes a display controller which causes at least one of the electrocardiogram data produced by the detector, the SpO2 measured by the detector, and the electromyogram data produced by the detector, to be displayed on a displaying section.

15. The magnetic stimulator according to claim 10, wherein the magnetic stimulator further includes a display controller which causes at least one of the electrocardiogram data produced by the detector, the SpO2 measured by the detector, and the electromyogram data produced by the detector, to be displayed on a displaying section.

16. A magnetic stimulation method comprising:
- applying magnetic stimulation to a head of a living body;
- controlling an intensity of the magnetic stimulation;
- acquiring a biological signal from the living body;
- detecting an adverse event of the living body from the acquired biological signal;
- suppressing the intensity of the magnetic stimulation when the adverse event of the living body is detected;
- acquiring an electrocardiogram signal of the living body;
- producing electrocardiogram data by using the acquired electrocardiogram signal;

predicting an epilepsy seizure by using the produced electrocardiogram data;
reducing the intensity of the magnetic stimulation, or stopping the magnetic stimulation, when the epilepsy seizure is predicted;
acquiring transmittances of blood of the living body with respect to red and infrared light beams;
measuring an arterial oxygen saturation (SpO2) by using the acquired transmittances;
stopping the magnetic stimulation when the measured SpO2 is equal to or less than a preset threshold; and
determining whether the SpO2 exceeds the preset threshold or not, when the epilepsy seizure is not predicted.

* * * * *